Figure 1:
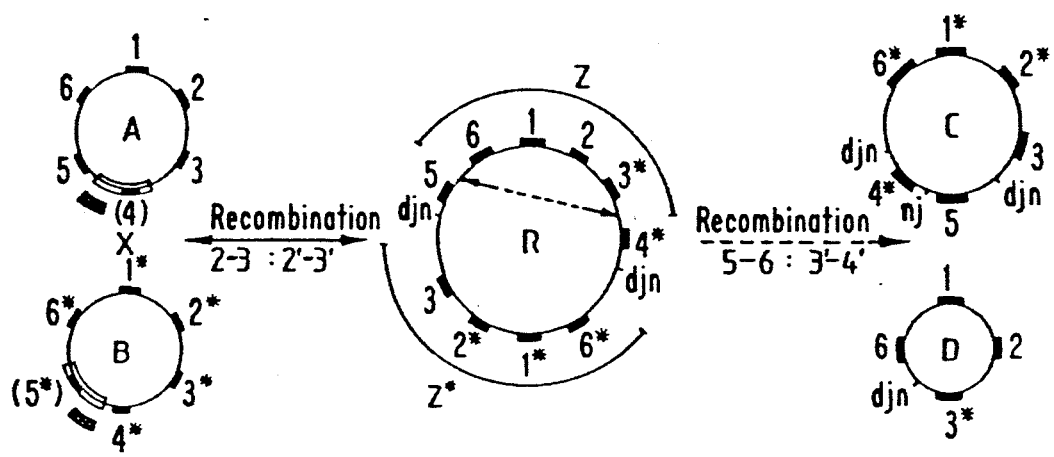

United States Patent [19]

Clark-Walker

[11] Patent Number: 5,073,489

[45] Date of Patent: Dec. 17, 1991

[54] METHOD FOR GENETICALLY MARKING YEAST

[75] Inventor: George D. Clark-Walker, Deakin, Australia

[73] Assignee: The Australian National University, Australian Capitol Territory, Australia

[21] Appl. No.: 485,767

[22] Filed: Feb. 26, 1990

Related U.S. Application Data

[63] Continuation of Ser. No. 94,729, filed as PCT/AU86/00357, Nov. 21, 1986, abandoned.

[30] Foreign Application Priority Data

Nov. 21, 1985 [AU] Australia ............................ 3512/85

[51] Int. Cl.$^5$ ...................... C12P 21/00; C07H 15/12; C12Q 1/68; C12N 1/18
[52] U.S. Cl. ..................................... 435/172.3; 435/6; 435/942; 435/255; 435/256; 935/29; 935/93; 935/97
[58] Field of Search ................ 435/172.1, 172.3, 255, 435/256, 254, 972, 6; 935/29, 93, 97

[56] References Cited

PUBLICATIONS

Evans, R. J. et al., Elevated Levels of Petite formation in Strains of *S. cerevisiae* Restored to Respiratory Competance III; and Genetics III, pp. 389–432 (1985).

Lang, B. F. et al., The Mitochondrial gernome of the fission yeast *S. pombe;* Mol. GenGenet 196, pp. 465–472 (1984).

Oakley, K. M. et al., Abnormal mitochondrial genomes in yeast restored to respiratory competence; Genetics 90(3), pp. 517–530.

Dujon B., Mitochondrial Genetics and Functions; in *The Molecular Biology of the Yeast Saccharomyces*, Cold Spring Harbor Press (1981), eds. Strathern, Jones, and Broach, pp. 505–542.

*Primary Examiner*—Robin L. Teskin
*Attorney, Agent, or Firm*—Bacon & Thomas

[57] ABSTRACT

A genetically marked strain of the yeast *Saccharomyces cerevisiae* is characterized in that the mitochondrial (mt)DNA of the yeast has been rearranged by recombination. A method of producing such a strain is also disclosed.

7 Claims, 1 Drawing Sheet

METHOD FOR GENETICALLY MARKING YEAST

This application is a continuation of application Ser. No. 094,729, filed as PCT/AU86/00357, Nov. 21, 1986, now abandoned.

This invention relates to a method of verifying or identifying microorganisms, and in particular it relates to verification or identification of the yeast Saccharomyces cerevisiae, a microorganism which is of great commercial significance.

Methods of verification or "finger-printing" of microorganisms have been developed which allow such organisms to be compared so as to provide positive information about the origin of organisms under test. In one such method, DNA from the organism under test is fragmented with a restriction endonuclease and the fragments are separated by gel electrophoresis. Specific fragments of DNA are revealed by hybridization with fragments of radio-actively labelled probes and the resulting pattern of hybridizing bands is a diagnostic characteristic for the organism under test. The commercial significance of such verification methods includes protection of novel inoculants in the agricultural and food industries; comparison of plant cell tissue culture lines and the plants grown from them; matching of new isolates of antibiotic-producers with previous, commercially successful organisms; and the cross-comparison of strains independently deposited in culture collections In addition, such verification methods may be used to ensure that genotypes are being maintained and cell lines are breeding true to type.

The present invention particularly relates to the unique identification by genetic marking or modification of yeast (Saccharomyces cerevisiae) which is used in the brewing, baking and biotechnology industries. A major concern of such industries is that valuable yeast strains may be pirated by competitors, and hence there is a need to be able to mark and identify commercially important strains of yeast. In general terms, the present invention provides a method whereby the gene order of mitochondrial (mt) DNA is rearranged to provide genetic marking. Such mtDNA markers are essentially "fingerprints" for the yeast strains containing them. The production of yeast strains with this rearranged gene order of mtDNA arises through a previously uncharacterised recombination pathway which is described in greater detail hereinafter. It is furthermore to be noted that strains having a rearranged gene order produced in accordance with the present invention do not occur in nature.

According to the present invention there is provided a method of identifying or genetically marking a strain of the yeast Saccharomyces cerevisiae, characterised in that the gene order of the mtDNA of said yeast is rearranged by recombination.

The present invention also extends to strains of the yeast Saccharomyces cerevisiae which are characterised in that the gene order of the mtDNA of the yeast has been rearranged by recombination.

In one aspect of this invention, there is provided a method of genetically marking the yeast Saccharomyces cerevisiae as broadly described above and other "petite-positive" species. Saccharomyces cerevisiae spontaneously produces respiratory deficient mutants (petites) at a high rate of approximately 1% per generation. This mutation is irreversible, cytoplasmically inherited, and associated with an element which has been identified as mitochondrial DNA. Petite mutants have large deletions from the circular 70-80 kbp mitochondrial genome. When recently arisen spontaneous petite mutants of S.cerevisiae are crossed, respiratory competent diploids can be recovered. Such restored strains can be divided into two groups having sectored or unsectored colony morphology, the former being due to an elevated level of spontaneous petite mutation. On the basis of petite frequency, the sectored strains can be subdivided into those with a moderate frequency (5-16%) and those with a high frequency (>60%) of petite formation.

The present invention arises from information which has been obtained from characterising abnormal mtDNAs in high and moderate frequency petite forming strains of S.cerevisiae, which has led to the proposal of a pathway for the generation of mtDNA sequence rearrangements. The studies just mentioned stem from the observation that a proportion of respiratory competent restored strains, obtained by mating recently arisen petites (Clark-Walker, G. D., Miklas, G. L. G., (1975) Proc.Natl.Acad.Sci. USA 72:372-375; Oakley, K. M., Clark-Walker, G. D. (1978) Genetics 40:517-530), show a high (hfp) (>60% petites/generation) or moderate (mfp) (5-16% petites/generation) frequency of petite mutants (Evans, R. J., Oakley, K. M., Clark-Walker, G. D. (1985) Genetics 111:389-402; Evans, R. J., Clark-Walker, G. D. (1985) Genetics 111:403 et.seq.). Characterisation of the abnormal mtDNAs in these strains has shown that hfp forms contain a like-oriented duplication that is prevented from rearranging to the parental type by a deletion in a non-essential region while the mfp class has mtDNA with an inverted duplication (op.cit.). It has now been discovered that with either type of abnormality rare recombinations remove the duplication in such a way that some of the resulting mtDNA molecules have an altered gene order.

FIG. 1 illustrates the possible mechanism for rearrangement of yeast mtDNA to produce a rearranged gene order. Deleted molecules A and B, containing a common region of deletion in a non-essential sequence (hatched segment), recombine in a region of homology (2-3:2'-3') to produce recombinant form R containing duplications (Z and Z*) in like orientation. Deletion by intramolecular recombination in the duplicated portions leads to reformation of the original defective molecules A and B. However, rare recombination events, analogous to ones producing deletions in wild-type mtDNA, (5-6:3'-4') could lead to formation of molecules C and D. Molecule C has a full complement of "genes" (segments 1-6) as well as novel structural features resulting from the two original deletion junctions (djn), a new junction (nj) and a rearrangement in segment order between 4 and 5.

To demonstrate the above-proposed mechanism involving a like-oriented duplication, non-sectoring colonies have been sought from hfp strains of S.cerevisiae and their mtDNAs examined. Growth of yeasts and preparation of mtDNA, have been described in detail in previous publications (Clark-Walker, G. D., McArthur, C. R., Deley, D. J. (1981), Curr Genet 4:7-12; McArthur, C. R., Clark-Walker, G. D. (1983) Curr Genet 7:39-35; Hoeben, P., Clark-Walker, G. D. (1985), Curr. Genet. 10, 371-379; Clark-Walker, G. D., McArthur, C. R., Sriprakash, K. S. (1983), J. Mol. Evol 19:333-341; and Clark-Walker, G. D., McArthur, C. R., Sriprakash, K. S. (1985) The EMBO Journal 4 465-473), and the detailed description in these publications is incorporated herein by reference. For the isolation of non-sectored colonies from the high frequency petite forming strains (hfp) of Saccharomvces cerevisiae, glycerol YP plates were spread at a density of approximately 200 respiratory competent colonies. After 2 weeks at 30°, plates were examined and putative non-sectoring colonies were subcultured onto glyYP plates Characterisation of mtDNA was performed by HhaI digestion of DNA obtained from whole cell lysates (Nasmyth, K. A., Reed, S. I. (1980) Proc.Natl.Acad.Sci.USA 77:2119-2123). Fragments were separated by electrophoresis in 1% agarose, transferred to nylon and mtDNA bands revealed by hybridization with labelled mtDNA from S.cerevisiae.

Figure 2:
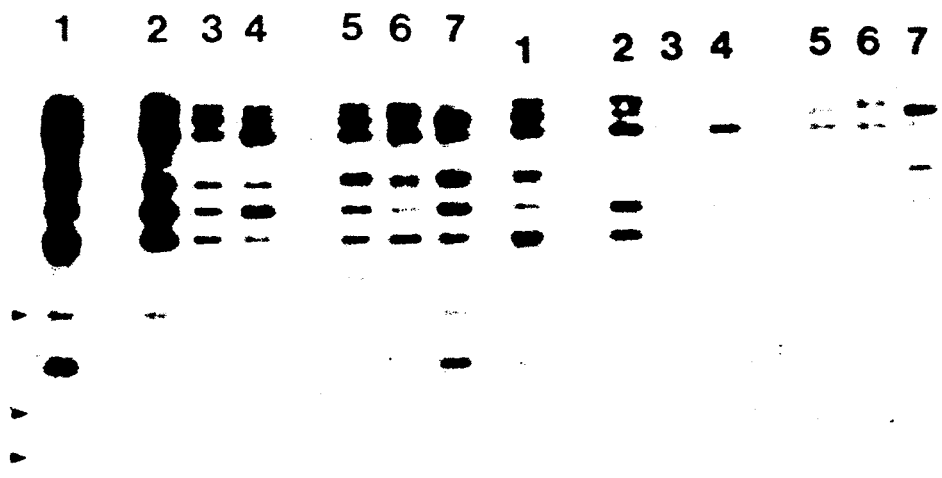

FIG. 2 is an autoradiogram produced by hybridization of [$^{32}$P] labelled mtDNA of S.cerevisiae to whole cell lysates digested with HhaI. Lanes contain DNA from (1) Diploid 2; (2) 15.19S; (3) 15.19R1; (4) 15.19EBr1; (5) 9.15S; (6) 9.15R5; (7) 9.15/1. The hybridization signals marked by arrows are present in rho° strains lacking mtDNA and may arise from nuclear encoded ribosomal DNA contaminating the mtDNA preparation used for the probe Different exposure times have been used to produce the two panels of the FIGURE.

For this demonstration hfp strains 15.19S and 9.15S were chosen (op.cit.). One non-sectored colony (15.19R1), with a petite frequency of 0.23% (Table 1), was found amongst 8500 sectored colonies of 15.19S and one non-sectored colony (9.15R5) of 9.15S, with a petite frequency of 2.6%, was found amongst 24,700 colonies. In addition one colony (9.15/1), derived from 9.15S, with a lowered petite frequency (56.0%) was obtained and one non-sectored isolate from 15.19S (15.19EBr1) was found after growth on plates containing 1ug/ml ethidium bromide.

absent. Other differences are the appearance of a novel band and the absence of a parental fragment (upper band of a doublet fourth from the top). Although unequivocal interpretation of mtDNA structure in 15.19R1 is to some extent hampered by non-stoiciometric hybridization as well as by co-migration of parental (15.19S) novel junction fragments with wild-type bands, nevertheless from mapping data for mtDNA of 15.19S (Evans, R. J., Clark-Walker, G.D. (1985) supra), the loss of the parental fragment mentioned above and the appearance of a new band (novel junction fragment) is consistent with excision of the duplication from the part of the molecule that does not contain the 2 novel junctions (FIG. 2). Thus, the mtDNA of 15.19R1 contains a rearrangement compared to the wild-type.

Of the two remaining isolates, 9.15/1 (lane 7) contains a duplication which now differs from the parental form. This change is associated with a high, yet altered level of petite production By contrast, the isolate obtained after ethidium bromide treatment has a normal petite frequency yet it still appears to contain a duplication (lane 4). It is possible that the mitochondrial genome in this isolate, under the influence of ethidium bromide, has undergone multiple recombination events so that an inverted duplication may now exist. As found for mfp strains, inverted duplications do not dramatically enhance the production of petite mutants (Evans, R. J., Oakley, K. M., Clark-Walker, G. D. (1985) supra; Evans, R. J., Clark-Walker, G. D. (1985) supra).

In conclusion it is envisaged that mtDNA rearrangements occur through a minimum of 3 steps. Firstly, wild-type mtDNA undergoes deletion events to produce defective molecules such as those found in petite mutants. This is followed by recombination between defective molecules to produce abnormal mtDNAs

TABLE 1

| Culture Petite Frequency (CPF) (%) in Sectored (S) and Unsectored Strains. | | | | | | |
|---|---|---|---|---|---|---|
| 1. | 2. | 3. | 4. | 5. | 6. | 7. |
| Strain Dip 2 | 15.19S | 15.19R1 | 15.19EBr1 | 9.15S | 9.15R5 | 9.15/1 |
| CPF % 0.45 | 87.0 | 0.23 | 0.25 | 72.0 | 2.6 | 56.0 |

Examination of mtDNA in whole cell lysates of these revertants shows that each has changed although characteristic features of the parental genomes are still present (FIG. 2). Analysis of mtDNA structure in 9.15R5 (lane 6) indicates that this genome has resulted from deletion of the duplication without alteration of gene order. Even though non-stoiciometric hybridization intensities of mtDNA fragments, as found in the wild-type (lane 1), complicates assessment of the results shown in FIG. 2, nevertheless comparison of band intensities at different exposure times leads us to suggest that mtDNA from 9.15R5 (lane 6) no longer contains a duplication. Other changes to this genome, in comparison to the parent (lane 5), are the absence of three fragments and the appearance of a novel fragment (second band from the top). These results demonstrate that a deletion event, spanning the two novel junctions in the mtDNA of 9.15S, has led to excision of the duplication as well as deletion of small amounts of flanking unique copy non-coding regions. Consequently the resulting mtDNA is now smaller than the wild-type but is not rearranged. On the other hand analysis of mtDNA in 15.19R1 (lane 3), the other spontaneous revertant showing a low petite frequency, indicates that this genome has a rearrangement. From the hybridization experiment, it appears that all of the duplicated bands are containing like-oriented duplications analogous to those which have been characterised in hfp strains. Finally, rare deletions occur to eliminate most or all of the duplication leaving a rearranged gene order as is demonstrated above has happened in the revertant 15.19R1. This final deletion step is again proposed to occur by the same process that produces petite mutants The key novel aspect of the above proposal leading to the basis for the present invention is that the recombinant form, containing the like-oriented duplication, cannot return to wild-type because of a deletion in a non-essential region.

In addition it has been found that recombinant mitochondrial DNAs, containing duplications, can be obtained by crossing strains having mitochondrial genomes each with a full complement of genes but with one having a rearrangement relative to the other. Among the products of such a cross are strains with recombinant mtDNAs similar to the ones obtaining by crossing recently arisen petite mutants described above.

It will be apparent to those skilled in the art that various modifications of the invention may be practised without departing from the present inventive concept. For example, making the nucleus of a yeast cell dependent upon its rearranged (marker) mtDNA will guard against attempts to replace the marker mtDNA.

I claim:

1. A method for genetically marking a strain of yeast *Saccharomyces cerevisiae* wherein said marking comprises the gene order of the mitochondrial DNA of the yeast which is rearranged by recombination; said method comprising:

crossing two respiratory deficient petite mutant strains of Saccharomyces cerevisiae wherein each of said respiratory deficient petite mutants has a region of deletion in the mitochondrial DNA; said region including a deleted segment which is essential for respiration and a deleted non-essential segment; said deleted non-essential segment being the same in both mutants and said deleted essential segment being different in each mutant; whereby said crossing produces a diploid strain wherein the genes common to both parents are duplicated and the deleted non-essential segment common to both parents is absent; and then recombining said diploid strain to remove one of each of the duplicated genes to form a genetically marked strain of yeast having a respiratory competent mitochondrial genome with a rearranged order of non-duplicated genes required for respiration relative to wild type and to the petite mutant parents and identifying and isolating said genetically marked strain of yeast with said rearranged order of mitochondrial genes from the recombinants produced.

2. A pure culture of yeast consisting essentially of a genetically marked yeast strain produced by the method of claim 1.

3. A pure culture of yeast consisting essentially of genetically marked strain of the yeast *Saccharomyces cerevisiae* having a full complement of non-duplicated genes required for respiration;

said genetically marked strain being produced by a method which includes crossing and recombining two respiratory deficient petite mutants of Saccharomyces cerevisiae whereby the said crossed and recombined strain has a respiratory competent mitochondrial genome with a full complement of non-duplicated genes required for respiration; said full complement of genes required for respiration being in rearranged order relative to wild-type and to the petite mutant parents; said rearranged order of genes serving as a genetic marker which is capable of being detected.

4. A method for genetically making a strain of the yeast *Saccharomyces cerevisiae* wherein the gene order of the ;mitochondrial DNA of the yeast is rearranged by recombination, said method comprising the steps of:

a. crossing two spontaneously produced respiratory deficient petite mutant strains of *Saccharomyces cerevisiae* to obtain respiratory competent diploid strains having sectored colony morphology and an elevated level of spontaneous petite mutation;

b. recovering said respiratory competent diploid strains, having an elevated level of spontaneous petite mutation;

c. isolating revertant strains having a normal level of petite mutation and which form non-sectoring colonies from the recovered strains;

d. characterizing the mitochondrial DNA of the isolated strains to determine which strains have a full complement of non-duplicated genes required for respiration and which full complement of genes required for respiration is in a rearranged order with respect to wild type and to the petite mutant parents;

e. selecting these strains in which the gene order is rearranged and culturing them to produce a culture of genetically marked strain of *Saccharomyces cerevisiae* wherein said genetic marking comprises the rearranged order of genes.

5. A pure culture of yeast consisting essentially of genetically marked strain of Saccharomyces cerevisiae produced by the method of claim 4.

6. A method of claim 4 wherein said characterization of the mitochondrial DNA of the isolated non-sectoring strains comprises the steps of digesting the DNA from all cell lysates; electrophoretically separating the DNA fragments and identifying the fragment pattern by hybridization with a labelled probe.

7. A pure culture of yeast consisting essentially of genetically marked strain of *Saccharomyces cerevisiae* produced by the method of claim 6.